(12) United States Patent
Kuhn et al.

(10) Patent No.: US 6,216,026 B1
(45) Date of Patent: Apr. 10, 2001

(54) METHOD OF NAVIGATING A MAGNETIC OBJECT, AND MR DEVICE

(75) Inventors: Michael Kuhn; Bernd Aldefeld, both of Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/136,649

(22) Filed: Aug. 19, 1998

(30) Foreign Application Priority Data

Aug. 20, 1997 (DE) ................................................ 197 36 030

(51) Int. Cl.[7] .................................................... A61B 5/05
(52) U.S. Cl. .................... 600/409; 600/422; 600/423; 600/431; 600/433; 606/130
(58) Field of Search .................................. 600/407, 409, 600/422, 431, 433, 423, 424, 417, 100, 101; 128/653.5, 899; 606/130; 324/260; 361/141

(56) References Cited

U.S. PATENT DOCUMENTS 5,353,795 * 10/1994 Souza et al. ...................... 128/653.2
5,654,864 * 8/1997 Ritter et al. .......................... 361/141
5,833,608 * 11/1998 Acker ................................... 600/409

FOREIGN PATENT DOCUMENTS

| 93666 | 3/1967 | (FR) . |
| 93666 | 3/1997 | (FR) . |
| 9603795A1 | 2/1996 | (WO) ............................. H02N/15/00 |
| WO9641119 | 12/1996 | (WO) . |

* cited by examiner

*Primary Examiner*—Marvin M. Lateef
*Assistant Examiner*—Jeoyuh Lin
(74) *Attorney, Agent, or Firm*—John F. Vodopia

(57) ABSTRACT

The invention relates to a method of navigating a magnetic object (11) within an object (1) which is exposed to a magnetic field, as well as to a magnetic resonance device in which this method can be carried out. The method according to the invention is particularly suitable for navigating a catheter or a flexible endoscope within the body of a patient. The magnetic object (11), preferably being provided in or on such a medical instrument (10), has a controllable magnetic moment for this purpose and the direction of movement of the object is determined by control of the magnetic moment. In the case of a magnetic resonance device whose static magnetic field is used, the object (11) is preferably includes as a coil system.

11 Claims, 2 Drawing Sheets

METHOD OF NAVIGATING A MAGNETIC OBJECT, AND MR DEVICE

BACKGROUND OF THE INVENTION

1. Field of the Invention

The invention relates to a method of navigating a magnetic object within an object to be examined which is exposed to a magnetic field. The invention also relates to a magnetic resonance (MR) device which includes a main field magnet system for generating a stationary, static magnetic field and a medical instrument, notably a catheter or a flexible endoscope, which is to be introduced into an object to be examined, a magnetic object being provided in or on the instrument.

2. Description of Related Art

A method of this kind is known from WO 9603795 A1. Therein, a passive magnetic object (a permanent magnet) is moved to given positions within the body of a patient by means of temporally and spatially varying magnetic fields which are generated by a plurality of notably superconducting coils. Therein, the motion is observed by means of X-rays.

An MR device of the kind set forth is disclosed in U.S. patent application Ser. No. 08/754,360. Therein, a microcoil attached to a catheter is used to observe the motion of the catheter within an object to be examined, for example by forming MR images from signals received from the microcoil.

It is an object of the invention to provide a method of navigating a magnetic object which is particularly suitable for magnetic resonance tomography. It is also an object of the invention to provide an MR device which is suitable for navigating a magnetic object.

The object in respect of the method is achieved in that the object has a controllable magnetic moment and that the direction of movement of the object is determined by control of the magnetic moment.

According to the invention, an active magnet (an electromagnet) is used generate the controllable magnetic moment which can notably be switched on and off. According to the known method, however, use is made of a passive magnet having an invariable magnetic moment; this is not suitable for MR tomography. The control of the direction of movement of the object utilizes the physical effect that an object having a magnetic moment in a magnetic field is subject to a mechanical moment whose direction and strength are dependent on the direction and the strength of the magnetic moment and of the magnetic field. In order to guide the object in a desired direction, according to the invention, a magnetic moment of suitable magnitude and direction is adjusted so that a mechanical moment occurs in the desired direction and with the required strength in the magnetic field present.

In preferred embodiment, each of three coils in the object can be individually supplied with a respective current, so that a magnetic moment can be adjusted in any arbitrary direction, thus enabling the object to be guided in any direction. The coils can receive a current simultaneously or consecutively.

A further embodiment of the invention is simple and space-saving. Because a magnetic moment cannot be adjusted in any direction when only one or two coils are used, this embodiment is provided with means, notably mechanical means such as joints and Bowden cables, in order to change the position of the individual coils or the coil system relative to the external magnetic field, and hence to change also the direction of the magnetic moment of a coil or the coil system. Each coil can again be supplied with a current individually or all coils can be supplied with a current simultaneously, and for an adjustable period of time, thus enabling adjustment of the desired magnetic moment.

The method according to the invention is preferably used in an MR device, the magnetic field then being the stationary, static magnetic field of the MR device. This magnetic field is notably also uniform and has a high magnetic field strength so that, even when use is made of a small coil, an adequate mechanical moment can be produced so as to guide the object in the magnetic field exclusively by means of the acting mechanical moment.

The method according to the invention is particularly suitable for moving a medical instrument, notably a catheter or a flexible endoscope, in an object to be examined, for example in the vascular system of the head of a patient. The mechanical instrument is then advanced, for example by hand, whereas a change of direction is realized by the method according to the invention.

In a further embodiment of the invention the position of the object can also be determined. This embodiment is used notably in an MR device and when the object is implemented as a coil system.

The object has a controllable magnetic moment and there are provided means for controlling the magnetic moment and for navigating the magnetic object within the object to be examined. These means may include, for example a suitable control unit and suitable current sources for supplying individual coils, preferably constituting the magnetic object, with currents for adjustment of a magnetic moment acting on the object.

BRIEF DESCRIPTION OF THE DRAWINGS

The invention will be described in detail hereinafter with reference to the drawings. Therein.

DETAILED DESCRIPTION OF THE PREFERRED EMBODIMENT

Figure 1:
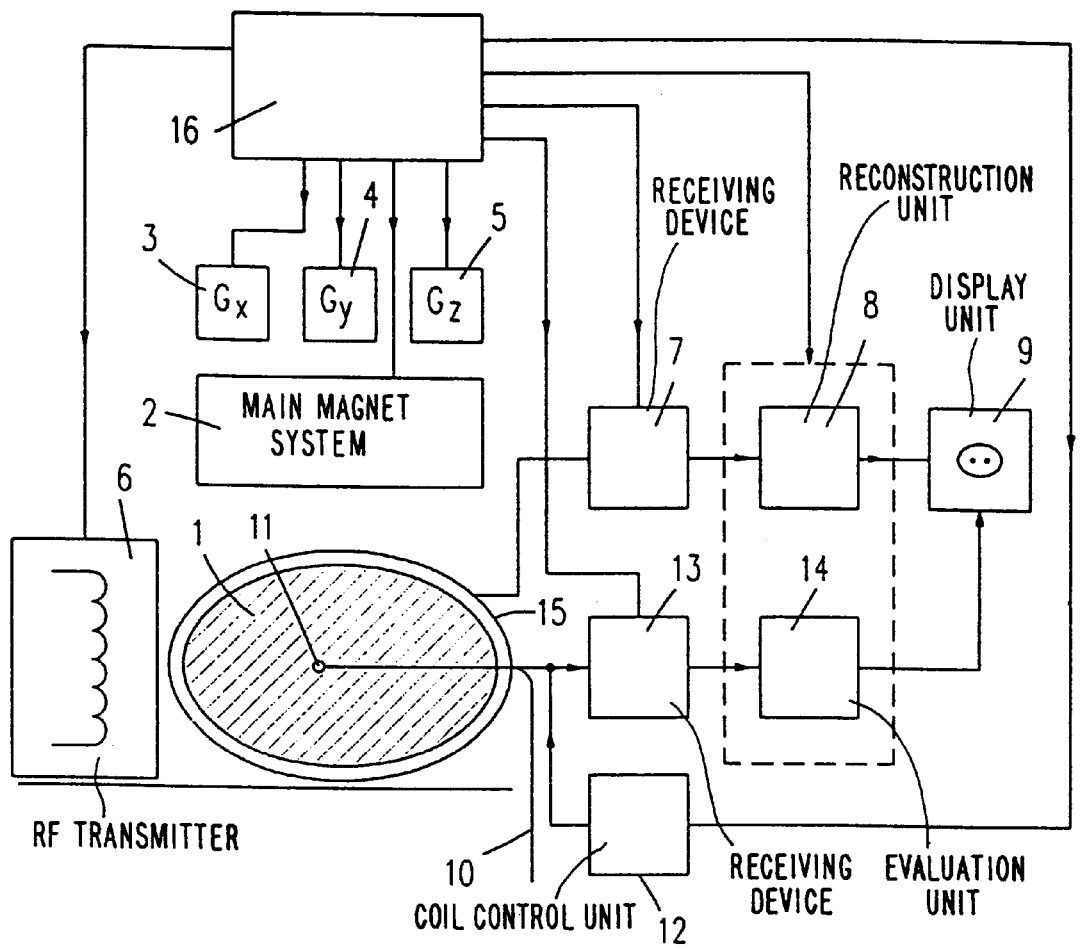
FIG. 1 shows a block diagram of an MR device according to the invention.

Referring to FIG. 1, an object 1 to be examined is arranged in an examination zone which is subject to a uniform, steady, static magnetic field which is generated by a main field magnet system 2. Magnetic gradient fields can be superposed on the uniform magnetic field by means of gradient coil systems 3, 4, 5. An RF transmitter 6 is capable of pulse-wise generating an RF magnetic field in the examination zone. MR signals generated in the object 1 to be examined are detected by a receiving coil system 15, in conjunction with a receiving device 7, and the nuclear magnetization distribution in the examination zone is reconstructed on the basis of the digitized MR signals, for example after a Fourier transformation, in a reconstruction unit 8, said nuclear magnetization distribution being displayed as an MR image on a display unit 9.

A medical instrument, for example a catheter 10 whose tip is provided with a coil 11 of small diameter (a microcoil), is introduced into the object 1 to be examined. The signals received by the coil 11 are applied to a receiving device 13 so as to be digitized and subsequently applied to an evaluation unit 14 which determines the position of the coil 11 and superposes it on the MR image displayed on the display unit 9. As is denoted by dashed lines, the components 8 and 14 can be implemented by way of a suitably programmed computer. The components 2 to 15 are controlled by a programmable control unit 16.

A coil control unit 12 controls the adjustment of the magnetic moment of the coil 11 when it is not switched to the receiving mode. To this end, the coil control unit 12 includes a current source which is capable of supplying the coil 11 with a direct current so as to generate a magnetic moment.

Figure 2:
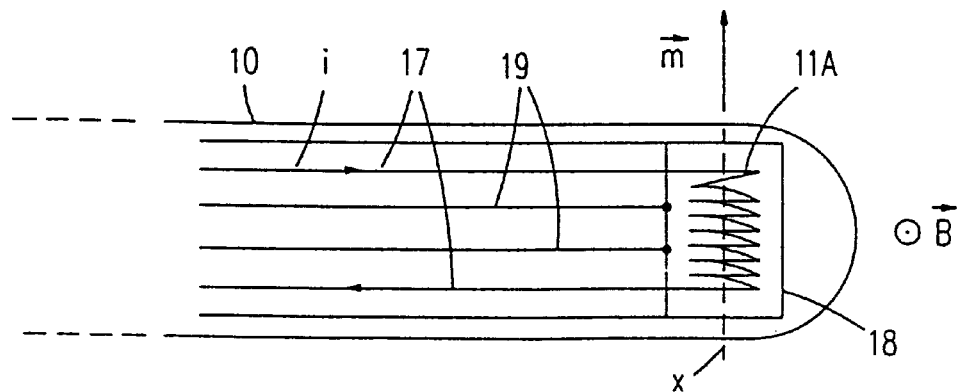
FIG. 2 shows a catheter provided with a first embodiment of a coil system.

A catheter 10, provided with a single cylindrical coil 11A, consisting of a plurality of turns, is shown at an increased scale in FIG. 2. The coil 11A can receive a current i via current leads 17 so that a magnetic moment $\vec{m}$ arises parallel to the longitudinal axis x: $\vec{m} = i.N.\vec{S}$, where i is the current flowing through the coil, N is the number of turns and $\vec{S}$ is the vector to the cross-sectional area of the coil having the radius $r(S=r^2.\pi)$. In a static magnetic field $\vec{B}$ in the direction shown, perpendicular to $\vec{m}$, the magnetic moment $\vec{M} = \vec{m} \times \vec{b}$ arises; its value is maximum when the magnetic field $\vec{B}$ extends perpendicularly to the magnetic moment $\vec{m}$ and has the value $$\max(|\vec{M}|) = \pi.i.N.r^2.|\vec{B}|.$$

The maximum force at the edge of the coil 11A amounts to approximately:

$$\max(F) = \max(|\vec{M}|)/r.$$

The mechanical moment thus ensures that the catheter 10 with the coil 11A is rotated about an axis which extends perpendicularly to the magnetic field $\vec{M}$ and perpendicularly to the axis extending perpendicularly to the magnetic moment $\vec{m}$, so in the direction of the mechanical moment $\vec{M}$.

In the case of a flux density of 1.5 T, a current of 1A and a coil having a radius of 1 mm and comprising ten turns, a maximum force amounting to 0.02 N occurs; this force suffices for guiding the catheter when use is made of an appropriately flexible catheter material.

In the embodiment shown in FIG. 2, the coil 11A is arranged in a sleeve 18 whereto mechanical pulling wires 19 are connected so as to change the position of the coil relative to the direction of the magnetic field $\vec{B}$. When the position of the coil 11A changes, the direction of the magnetic moment $\vec{m}$ is also changed, so that the resultant mechanical moment also has a different direction and a force acts on the tip of the catheter 10 in a different direction.

Figure 3:
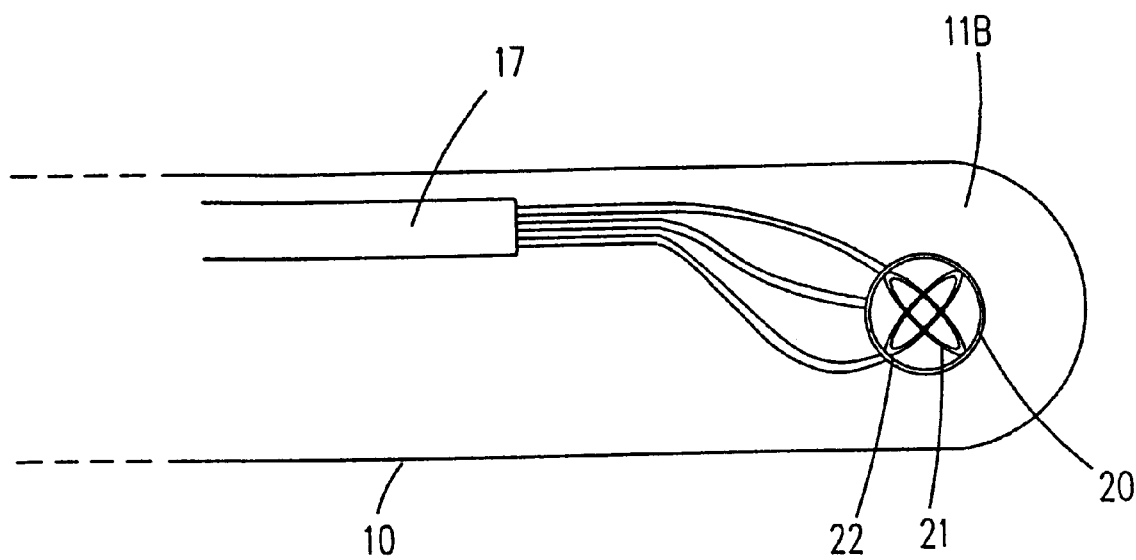
FIG. 3 shows a catheter provided with a second embodiment of a coil system.

FIG. 3 shows an alternative embodiment of a catheter 10. The coil system 11B thereof consists of three coils 20, 21, 22 which are arranged perpendicularly to one another about a common center; each coil may consist of a plurality of turns. Via a supply lead 17, each of the three coils 20, 21, 22 can individually receive a respective current for adjustment of a magnetic moment in such a manner that a mechanical moment occurs in the desired direction in the outer magnetic field. The coils 20, 21, 22 can then receive, simultaneously or temporally consecutively, a current of the required value and for the required period of time.

Figure 4:
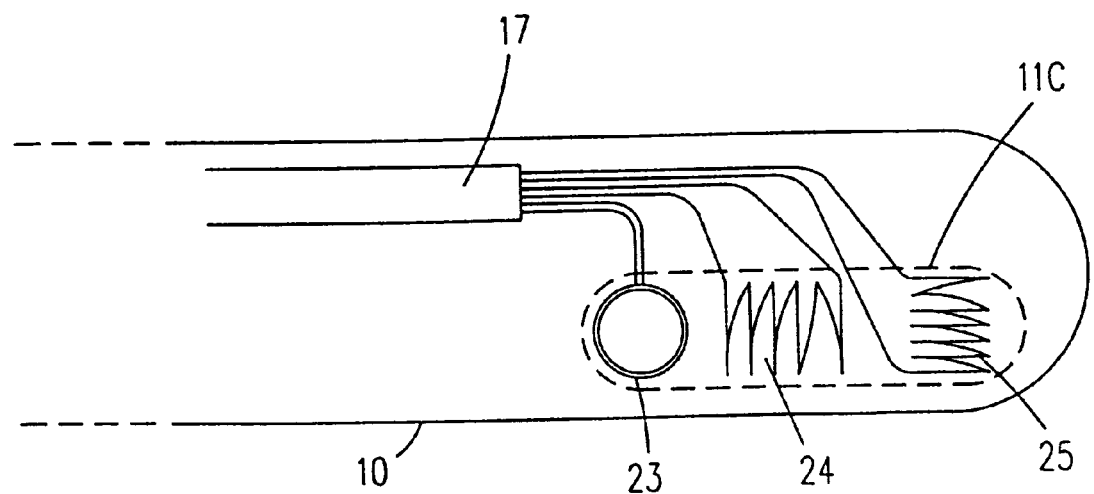
FIG. 4 shows a catheter provided with a third embodiment of a coil system.

FIG. 4 shows a further alternative embodiment in which the coil system 11C also consists of three mutually perpendicularly arranged coils 23, 24, 25 which, however, are arranged one behind the other in the catheter 10.

Instead of using the annular solenoid coils shown, use can be made of saddle coils which are arranged on a cylindrical member at the tip of the catheter. In order to change the position of a coil or the tip of the catheter, instead of said mechanical pulling wires use can be made of materials which assume a given position or curvature as soon as a counter force disappears. The use of special catheters (for example, pigtail catheters), in which a soft, curved wire is moved forwards from a comparatively rigid sleeve so that it can reach a given position or direction, is also feasible.

The coil 11 (see FIG. 1) can be capable of receiving signals (for determining the position of the coil) as well as of moving the catheter within the object to be examined. Alternatively, it is possible to provide several coils for separate purposes.

The invention is used particularly for navigating a catheter in the vascular system of the head, for example in order to dissolve a blood clot in a vessel. To this end, the catheter must be moved from a main vessel into the correct secondary vessel, necessitating local bending of the catheter tip. The vascular system can be imaged in advance, for example by means of an MR angiography method.

What is claimed is:

1. A method of controlling a direction of movement of a magnetic object in a field by altering a controlled magnetic moment of the magnetic object.

2. A method as claimed in claim 1, wherein the alteration of the controlled magnetic moment of the magnetic object is performed using a coil system which includes three mutually orthogonal coils.

3. A method as claimed in claim 1, wherein the alteration of the controlled magnetic moment of the magnetic object is performed using a coil system which includes one of two mutually orthogonal coils so that a position of the coil system is changed relative to the magnetic field.

4. A method as claimed in claim 2, wherein control of the direction of movement of the magnetic object further comprises applying a current to the coil system.

5. A method as claimed in claim 1, wherein the controlling the direction of movement of the magnetic object in the field further comprises controlling a direction of movement of the magnetic object in a magnetic field of a magnetic resonance device.

6. A method as claimed in claim 1, wherein the magnetic object is arranged in or on a medical instrument.

7. A method as claimed in claim 1, wherein the magnetic object is arranged to generate and/or detect a magnetic field and wherein the position of the magnetic object is determined by utilizing the magnetic field generated or detected by the magnetic object.

8. A magnetic resonance device comprising a main field magnetic system for generating a magnetic field, a medical instrument introduced into an object to be examined by the magnetic resonance device, and a magnetic object disposed in or on the medical instrument, wherein the magnetic object has a controllable magnetic moment and wherein there are provided means for controlling the magnetic moment and for navigating the magnetic object within the object to be examined.

9. The method of claim 3, wherein control of the direction of movement of the magnetic object further comprises applying a current to the coil system.

10. The method of claim 6, wherein the magnetic object is arranged in or on a catheter.

11. The magnetic resonance device of claim 8 wherein the medical instrument is a catheter or a flexible endoscope.

* * * * *